(12) United States Patent
Lemire et al.

(10) Patent No.: US 10,393,713 B2
(45) Date of Patent: Aug. 27, 2019

(54) METHOD FOR OPERATING A PROBE

(71) Applicant: CONTINENTAL AUTOMOTIVE GMBH, Hannover (DE)

(72) Inventors: Bertrand Lemire, Schierling (DE); Johannes Bentner, Pentling (DE); Sabrina Kolbeck, Eschlkam (DE); Muammer Kilinc, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 141 days.

(21) Appl. No.: 15/718,982

(22) Filed: Sep. 28, 2017

(65) Prior Publication Data

US 2018/0017537 A1  Jan. 18, 2018

Related U.S. Application Data

(63) Continuation of application No. PCT/EP2016/056677, filed on Mar. 24, 2016.

(30) Foreign Application Priority Data

Apr. 1, 2015 (DE) .......................... 10 2015 205 971

(51) Int. Cl.
  *G01N 33/00* (2006.01)
  *G01N 27/417* (2006.01)
  (Continued)

(52) U.S. Cl.
  CPC ...... *G01N 33/0006* (2013.01); *G01M 15/104* (2013.01); *G01N 27/417* (2013.01);
  (Continued)

(58) Field of Classification Search
  None
  See application file for complete search history.

(56) References Cited

U.S. PATENT DOCUMENTS 6,290,829 B1  9/2001 Kato et al.
2003/0079521 A1* 5/2003 Bolz ................. G01N 27/4065
                                                            73/23.31
(Continued)

FOREIGN PATENT DOCUMENTS

DE     10036129 A1    2/2002
DE     69732582       5/2006
(Continued)

OTHER PUBLICATIONS

International Search Report and Written Opinion dated Jul. 11, 2016 from corresponding International Patent Application No. PCT/EP2016/056677.
(Continued)

*Primary Examiner* — Peter J Macchiarolo
*Assistant Examiner* — Mohammed E Keramet-Amircolai

(57) ABSTRACT

A method for operating a probe having a pumped reference cell. A pulse-width-modulated pump current is applied to the reference cell at a first point in time. In accordance with the first point in time, a first voltage characteristic value (representing the voltage applied to the reference cell) is determined within a first time frame. The pulse-width-modulated pump current applied to the reference cell is switched off at a second point in time. A third point in time is determined, at which a pulse-width-modulated pump current applied to the reference cell is switched off. In accordance with the third point in time, a second voltage characteristic value (representing the voltage applied to the reference cell) is determined within a second time frame. The first and second voltage characteristic values are used to determine a diagnostic characteristic value, which is representative of an error in determining the nitrogen oxide concentration.

11 Claims, 2 Drawing Sheets

(51) Int. Cl.
*G01N 27/419* (2006.01)
*G01M 15/10* (2006.01)
*F01N 11/00* (2006.01)
*F02D 41/14* (2006.01)
*F02D 41/22* (2006.01)
*F01N 13/00* (2010.01)

(52) U.S. Cl.
CPC ....... *G01N 27/419* (2013.01); *G01N 33/0037* (2013.01); *F01N 11/007* (2013.01); *F01N 13/008* (2013.01); *F01N 2560/025* (2013.01); *F01N 2560/026* (2013.01); *F02D 41/146* (2013.01); *F02D 41/222* (2013.01); *Y02A 50/245* (2018.01)

(56) References Cited

U.S. PATENT DOCUMENTS

| | | | | |
|---|---|---|---|---|
| 2003/0080003 | A1* | 5/2003 | Akhavan | G01N 27/4175 205/784.5 |
| 2003/0101796 | A1* | 6/2003 | Bolz | G01N 27/4065 73/23.31 |
| 2005/0061684 | A1* | 3/2005 | Bausewein | G01N 27/406 205/785.5 |
| 2008/0314023 | A1* | 12/2008 | Pohmerer | F01N 11/007 60/285 |
| 2012/0097553 | A1* | 4/2012 | Classen | G01N 27/4074 205/781 |
| 2013/0234744 | A1* | 9/2013 | Carbonaro | G01M 15/104 324/750.03 |
| 2013/0263652 | A1* | 10/2013 | Fey | G01M 15/104 73/114.73 |
| 2014/0007644 | A1* | 1/2014 | Fey | G01N 33/0006 73/1.06 |
| 2014/0358403 | A1* | 12/2014 | Brinkmann | G01M 15/104 701/103 |
| 2015/0135802 | A1* | 5/2015 | Fey | F02D 41/1454 73/23.21 |
| 2016/0011077 | A1* | 1/2016 | Horn | F02D 41/123 73/114.73 |
| 2016/0201588 | A1* | 7/2016 | Bevot | F02D 41/28 73/114.73 |
| 2016/0327512 | A1* | 11/2016 | Reinhardt | G01N 27/4065 |

FOREIGN PATENT DOCUMENTS

| | | |
|---|---|---|
| DE | 102008024177 B3 | 9/2009 |
| DE | 102008042268 A1 | 4/2010 |
| DE | 102010030117 A1 | 12/2011 |
| DE | 102011089383 A1 | 6/2013 |
| DE | 102012200038 A1 | 7/2013 |
| DE | 102014205383 A1 | 10/2015 |
| WO | 2010020641 A1 | 2/2010 |

OTHER PUBLICATIONS

German Office Action dated Apr. 12, 2015 for corresponding German Patent Application No. 10 2015 205 9715.

* cited by examiner

METHOD FOR OPERATING A PROBE

CROSS-REFERENCE TO RELATED APPLICATIONS

This application claims the benefit of PCT Application PCT/EP2016/056677, filed Mar. 24, 2016, which claims priority to German Application DE 10 2015 205 971.5 filed Apr. 1, 2015. The disclosures of the above applications are incorporated herein by reference.

FIELD OF THE INVENTION

The invention concerns a method for operating a probe with a pumped reference cell.

BACKGROUND OF THE INVENTION

Probes for detecting a concentration of a gas from a gas mixture are widely used nowadays. In particular, in modern vehicles probes may be used in order to determine a concentration of a gas in the combustion exhaust gas for example.

SUMMARY OF THE INVENTION

The object of the invention is to provide a method for operating a probe with a pumped reference cell that contributes to the reliable and precise operation of the probe.

The object is achieved by the independent claim. Advantageous embodiments are characterized in the subordinate claims.

The invention is characterized by a method for operating a probe with a pumped reference cell. A first point in time is determined at which a pump current applied to the reference cell is turned on. Depending on the first point in time, at least one first voltage characteristic value that is representative of a voltage applied to the reference cell is determined within a predetermined first time window. The pump current applied to the reference cell is turned off at a second point in time. A third point in time is determined at which a pump current applied to the reference cell is turned off. Depending on the third point in time, at least one second voltage characteristic value that is representative of the voltage applied to the reference cell is determined within a predetermined second time window. A diagnostic characteristic value that is representative of an impedance of the reference cell is determined as a function of the at least one first voltage characteristic value and the at least one second voltage characteristic value.

This has the advantage that an electrical diagnosis of an impedance of the reference cell may be carried out. In particular, the diagnosis may be a self-diagnosis of the probe during the operation of the probe. For this purpose, a corresponding precaution may be dispensed with when designing the pump current, i.e. an amplitude of the pump current is unchanged at a high level, whereby a reference air contamination (also known as "chemical shift down") may be avoided. Furthermore, the self-diagnosis may in particular be carried out free of complex boundary conditions, which could only be achieved for example by dismantling the probe. This enables a defective probe with an excessively aged cell impedance to be detected in the field, for example.

The probe is in particular a probe for determining a gas concentration from a gas mixture. In particular, the probe is operated amperometrically for this purpose. For example, the probe is a nitrogen oxide sensor or an oxygen sensor.

The first point in time corresponds for example to a starting time of a self-diagnosis of the probe. In this case, the second point in time is after the first point in time. Alternatively for this purpose, the second point in time corresponds to a starting time of the self-diagnosis of the probe, wherein the first point in time is after the second point in time. This is in particular the case if it is ensured that the voltage applied to the reference cell is representative of a valid self-diagnosis of the probe.

The impedance of the reference cell represented by the diagnostic characteristic value may cause an error in a measurement result of the probe. In this connection, depending on the at least one first voltage characteristic value and the at least one second voltage characteristic value an assessment is carried out that is incorporated in the diagnostic characteristic value for self-diagnosis. The diagnostic characteristic value may, in this connection, also be used as a measure of a sensitivity.

Of the probe, for example as a measure of a nitrogen oxide sensitivity and/or an oxygen sensitivity of the probe and/or as a measure of a state of the probe, such as for example "good" or "poor".

In an advantageous embodiment, a wait phase for a predetermined first period of time is carried out between the second point in time and the third point in time. This has the advantage that the at least one second voltage characteristic value that is determined in the second predetermined time window is substantially stable, which means that the voltage applied to the reference cell is essentially in a steady state. Advantageously, this contributes to high precision of the at least one determined second voltage characteristic value.

In a further advantageous embodiment, the pump current applied to the reference cell is turned on at a fourth point in time. The fourth point in time is after the third point in time. Advantageously, this helps to ensure that the voltage applied to the reference cell is stable until the fourth point in time during determination of the at least one second voltage characteristic value.

In a further advantageous embodiment, a fifth point in time is determined at which a pump current applied to the reference cell is turned on. The fifth point in time is after the fourth point in time. Depending on the fifth point in time, at least one third voltage characteristic value that is representative of the voltage applied to the reference cell is determined within a predetermined third time window. This enables the verification of whether the voltage applied to the reference cell is representative of a valid self-diagnosis of the probe.

In a further advantageous embodiment, a wait phase for a predetermined second period of time is carried out between the fourth point in time and the fifth point in time. This has the advantage that the at least one third voltage characteristic value determined in the third predetermined time window is essentially stable, which means that the voltage applied to the reference cell is substantially in a steady state. Advantageously, this contributes to high precision of the at least one determined third voltage characteristic value.

In a further advantageous embodiment, the diagnostic characteristic value is determined depending on the at least one third voltage characteristic value. This is used as a particularly precise and reliable determination of the diagnostic characteristic value.

In a further advantageous embodiment, determination of the diagnostic characteristic value includes the determination of a difference as a function of the respective voltage characteristic values. This enables a simple determination of the diagnostic characteristic value. For example, the determination of the diagnostic characteristic value comprises the determination of the difference of the at least one first voltage characteristic value and of the at least one second voltage characteristic value.

In a further advantageous embodiment, the determination of the diagnostic characteristic value comprises the determination of an average value as a function of the respective voltage characteristic values. This enables a particularly simple determination of the diagnostic characteristic value. For example, the determination of the diagnostic characteristic value comprises the determination of the difference of respective average values of the at least one first voltage characteristic value and of the at least one second voltage characteristic value. Alternatively or additionally, a different signal filtering from the determination of the average value is carried out.

In a further advantageous embodiment, the determination of the diagnostic characteristic value comprises the determination of a standard deviation as a function of the respective voltage characteristic values. This enables simple verification of whether the voltage applied to the reference cell is representative of a valid self-diagnosis of the probe. In this connection, this contributes to precise and reliable determination of the diagnostic characteristic value. For example, for this purpose the first voltage characteristic value is compared with the third voltage characteristic value, so that drifting of the voltage applied to the reference cell during the diagnosis may be checked. In particular, in this case the difference of the first voltage characteristic value and of the third voltage characteristic value is determined. Depending on the comparison, by way of example an assessment is carried out in relation to the validity of the self-diagnosis.

In a further advantageous embodiment, the probe comprises a measurement cell. A target voltage characteristic value that is representative of a voltage applied to the measurement cell for measuring a gas concentration of a gas mixture delivered to the probe is determined as a function of the diagnostic characteristic value. A current applied to the measurement cell is controlled such that the voltage applied to the measurement cell is set to the target voltage characteristic value.

Advantageously, this enables compensation of the impedance of the reference cell. The current applied to the measurement cell is in this connection representative of the gas concentration of the gas mixture delivered to the probe. A determination of the target voltage characteristic value as a function of the diagnostic characteristic value may also be referred to as compensation of a target value of the Nernst voltage. Alternatively or additionally, the probe may in particular comprise a plurality of measurement cells, wherein depending on the diagnostic characteristic value a common or separate compensation of respective target values of the Nernst voltages is carried out, for example.

In a further advantageous embodiment, the probe is implemented as or comprises an oxygen sensor. The oxygen concentration of a gas mixture delivered to the oxygen sensor is determined as a function of the diagnostic characteristic value. For example, a determination of correction parameters is carried out in this connection as a function of the diagnostic characteristic value, so that correct operating points of the oxygen sensor are set and a variation of the impedance of the reference cell may be compensated. The determined oxygen concentration may in particular be a corrected oxygen concentration.

In a further advantageous embodiment, the probe is disposed as a nitrogen oxide sensor in an exhaust duct of an internal combustion engine. A nitrogen oxide concentration of a gas mixture delivered to the oxides of nitrogen sensor is determined as a function of the diagnostic characteristic value. The determination of the first point in time is carried out depending on an operating state of the internal combustion engine. The operating state of the internal combustion engine in which the first point in time is determined may for example consist of one of the following: partial load, engine braking, overrun and the $\Delta=1$ operating point. Advantageously, this contributes to particularly precise and reliable determination of the diagnostic characteristic value. In particular, it is assumed that a substantially stable voltage is applied to the reference cell in the case of the aforementioned operating states.

Moreover, a determination of correction parameters is optionally carried out, for example as a function of the diagnostic characteristic value, so that correct operating points of the oxides of nitrogen sensor may be set and a variation of the impedance of the reference cell may be compensated.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Exemplary embodiments are described in detail below using the schematic figures. In the figures.

DETAILED DESCRIPTION OF THE PREFERRED EMBODIMENTS

The following description of the preferred embodiment(s) is merely exemplary in nature and is in no way intended to limit the invention, its application, or uses.

Figure 1:
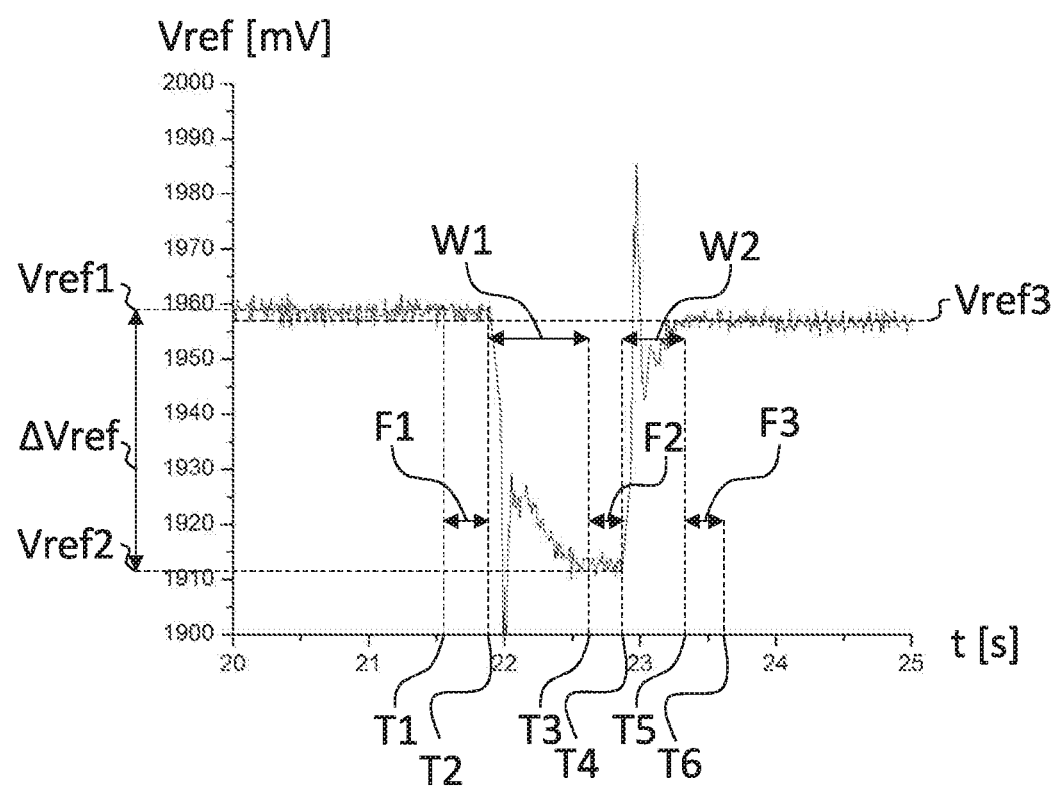
FIG. 1 shows a profile of a reference voltage of a reference cell of a probe in a schematic representation.

Probes for detecting a concentration of a gas from a gas mixture are widely used nowadays. In particular, in modern vehicles probes are used in order to determine a residual oxygen concentration in the combustion exhaust gas for example, and/or a nitrogen oxide concentration in the combustion exhaust gas. In this case, often part of the probe is exposed to the combustion exhaust gas while reference oxygen is applied to a further part of the probe. In this connection, the probe may comprise a pumped reference cell that provides the oxygen reference depending on a pump current that is applied to the reference cell. FIG. 1 shows a profile of a reference voltage Vref of such a pumped reference cell during the operation of an amperometrically operated oxides of nitrogen probe that is disposed in the exhaust duct of a vehicle, plotted against the time t. The reference cell constitutes the reference point for all oxygen concentrations measured in the probe. For this purpose, a Nernst voltage is measured. The reference cell is controlled by means of a pulse width modulated (PWM) current, for example.

In the profile represented, the reference voltage Vref has a value of about 1960 mV through a first point in time T1 to a second point in time T2. In this period of time, the reference cell is in a pumped operating state. The pumped operating state is implemented by applying a direct current and also a pulse width modulated current to the reference cell. In the profile represented, the reference voltage Vref is measured in particular during the switched-off time of the pulse width modulated current, i.e. not during one of the pulses of the pulse width modulated current. In this connection, the pulse width modulated current may also be referred to as the pump current.

Between the second point in time T2 through a third point in time T3 to a fourth point in time T4, the reference voltage Vref fluctuates strongly and settles finally at about 1910 mV. In this period of time, the reference cell is in an unpumped operating state. In this case, for example the pulse width modulated current may adopt a minimum magnitude, for example 0 A.

Between the fourth point in time T4 through a fifth point in time T5 to a sixth point in time T6, the reference voltage Vref fluctuates initially strongly and finally settles at about the initial value of 1960 mV. The reference cell is in pumped operating state during the aforementioned period of time.

The Nernst voltage of the measurement cavities in the probe are preferably measured in a deenergized state of the reference cell, i.e. when a PWM current pulse has decayed. Otherwise, the Nernst voltage may be corrupted by the ohmic voltage drop. This would for example result in the probe operating at a false operating point that deviates from the original calibration, and consequently a false oxides of nitrogen concentration would be output.

In particular, this may be the case if the reference cell comprises a capacitive component as well as the purely ohmic component. For example, in the case of reference cells comprising yttrium stabilized zirconium oxide, the impedance of the reference cell may increase strongly through ageing. Depending on the impedance of the reference cell and the resulting decay time after switch-off of the PWM pulse, the measurement may be distorted.

By a measurement of a difference ΔVref of the reference voltage Vref between the pumped operating state of the reference cell and the unpumped operating state of the reference cell, it is determined during a self-diagnosis of the probe whether the reference voltage Vref has essentially fully relaxed or there is a voltage offset because of an excessive impedance of the reference cell.

A computer program for operating the probe is described in detail below using the flow chart of FIG. 2 and in connection with the represented profile of FIG. 1, which is implemented to carry out a method according to the general part of the description when executed on a data processing device. In particular, the program is used for the self-diagnosis of the probe.

The program is started in a step S1, in which for example variables are initialized. At this point in time the profile the reference voltage Vref may for example already exist. Alternatively for example, the program may be executed in real time.

In a step S3, the first point in time T1 is determined at which the pump current applied to the reference cell is turned on. The first point in time T1 corresponds in particular to a starting time of the self-diagnosis of the probe. The first point in time T1 may be selected depending on an engine operating state, for example. For example, the self-diagnosis is carried out in one of the engine operating states partial load, engine braking, overrun or the Δ=I operating point. The operating states are particularly suitable for self-diagnosis of the probe, because fluctuations of the reference voltage Vref essentially depend only on the pump current.

Furthermore, the second point in time T2 is determined, that is separated in time by a period of time corresponding to a predetermined first time window F1 (cf. FIG. 1). The predetermined first time window F1 lasts between 0.2 s and 2 s, for example. Within the predetermined first time window F1, i.e. between the first point in time T1 and the second point in time T2, an average value and a standard deviation of the reference voltage Vref are determined. The average value determined during this is assigned to a first voltage characteristic value Vref1 (cf. FIG. 1). The program is then continued in a step S5.

In the step S5, a check is made as to whether the standard deviation determined in the step S3 lies within a predetermined limit within the predetermined first time window F1, i.e. does not exceed a predetermined first threshold value. In particular, this is used for a check of whether the measured reference voltage is stable within the predetermined first time window F1 before the pump current is then turned off. In the case in which the predetermined first threshold value is not exceeded, the program is continued in a step S7. Otherwise, the program is continued in a step S25.

In the step S7, the pump current is turned off corresponding to the second point in time T2. The program is then continued in a step S9.

In the step S9, a wait phase for a predetermined first period of time W1 (cf. FIG. 1) is carried out. The predetermined first period of time W1 extends from the second point in time T2 to the third point in time T3 here. This enables the decay of the reference voltage Vref. From the third point in time T3, a stable reference voltage Vref may be expected. The predetermined first period of time W1 lasts for example between 0.5 s and 1 s for this purpose. The program is then continued in a step S11.

In the step S11, the third point in time T3 is determined at which the pump current applied to the reference cell is turned off. Furthermore, the fourth point in time T4 is determined that follows the third point in time T3 and is separated in time by a period of time corresponding to a predetermined second time window F2 (cf. FIG. 1). The predetermined second time window F2 lasts between 0.2 s and 2 s, for example. Within the predetermined second time window F2, i.e. between the third point in time T3 and the fourth point in time T4, again an average value as well as a standard deviation of the reference voltage Vref are determined. The average value determined hereby is assigned to a second voltage characteristic value Vref2 (cf. FIG. 1). The program is then continued in a step S13.

In the step S13, the pump current corresponding to the fourth point in time T4 is turned on. The program is then continued in a step S15.

In the step S15, a wait phase for a predetermined second period of time W2 is carried out (cf. FIG. 1). The predetermined second period of time W2 extends from the fourth point in time T4 to the fifth point in time T5 here. This enables the decay of the reference voltage Vref. From the fifth point in time T5, a stable reference voltage Vref is expected. The predetermined second period of time W2 lasts for example between 0.5 s and 1 for this purpose s. In particular, in this case the predetermined second period of time W2 is longer than the first period of time W1. The program is then continued in a step S17.

In the step S17, the sixth point in time T6 is determined at which the pump current applied to the reference cell is turned on. In this case, the sixth point in time T6 is after the fifth point in time T5. In particular, in this case the sixth point in time T6 is separated from the fifth point in time T5 by a predetermined third time window F3 (cf. FIG. 1). The predetermined third time window F3 lasts between 0.2 s and 2 s, for example. Within the predetermined third time window F3, i.e. between the fifth point in time T5 and the sixth point in time T6, again an average value as well as a standard deviation of the reference voltage Vref are determined. The average value determined hereby is assigned to a third voltage characteristic value Vref3 (cf. FIG. 1). The program is then continued in a step S19.

In the step S19, a check is made of whether the standard deviation determined in the step S17 lies within a predetermined limit during the predetermined third time window F3, i.e. a predetermined second threshold value is not exceeded. The predetermined second threshold value may for example coincide with the predetermined first threshold value. In particular, this is used to check whether the measured reference voltage is stable within the predetermined third time window F3 after the pump current has been turned on. In the case in which the predetermined second threshold value is not exceeded, the program is continued in a step S21. Otherwise, the program is continued in the step S25.

In the step S21, a check is made of whether a difference between the first voltage characteristic value Vref1 and the third voltage characteristic value Vref3 lies within a predetermined limit, i.e. a predetermined third threshold value is not exceeded. In particular, this is used for verification of whether the measured reference voltage Vref between the first point in time T1 and the sixth point in time T6 is representative of a valid diagnosis. In the case in which the predetermined third threshold value is not exceeded, the program is continued in a step S23. Otherwise, the program is continued in the step S25.

In the step S23, a difference ΔVref between the first voltage characteristic value Vref1 and the second voltage characteristic value Vref2 is determined. Depending on the difference ΔVref, a diagnostic characteristic value D is determined. The diagnostic characteristic value D is representative of the impedance of the reference cell. This may cause a deviation of the oxides of nitrogen concentration in the combustion exhaust gas detected by the probe. The diagnostic characteristic value D is consequently representative of an error in the determination of the oxides of nitrogen concentration. There is approximately a linear relationship here. For example, a determination of the error as a function of the difference ΔVref between the first voltage characteristic value Vref1 and the second voltage characteristic value Vref2 is carried out in this connection. In this case for example, a voltage offset caused by an excessive impedance of the reference cell undergoes an assessment, which as a diagnostic result is incorporated into the diagnostic characteristic value D. The diagnostic characteristic value D may in particular be output, for example to a bus system of the vehicle such as the CAN-Bus. The diagnostic result may either adopt a binary value such as "good" or "poor", or even a continuous percentage value that indicates an expected deviation from a calibrated state of the probe. This advantageously enables an engine control unit to detect the state of the probe in the field, i.e. during the operation of the vehicle, and without having to seek a workshop for this purpose. In this case, in particular it may be determined whether a measurement accuracy of the probe is still sufficient to control an exhaust system of the vehicle.

Optionally, furthermore compensation of the target values of the Nernst voltages are carried out, so that the oxides of nitrogen concentration may continue to be precisely and reliably determined, even in the case of aging of the probe. During this, a correction parameter is determined from the diagnostic result that enables correct operating points of the probe to be set and thereby compensation of the impedance variation through ageing or alteration. The program is then ended.

In the step S25, the self-diagnosis is terminated. The program is then ended.

Figure 2:
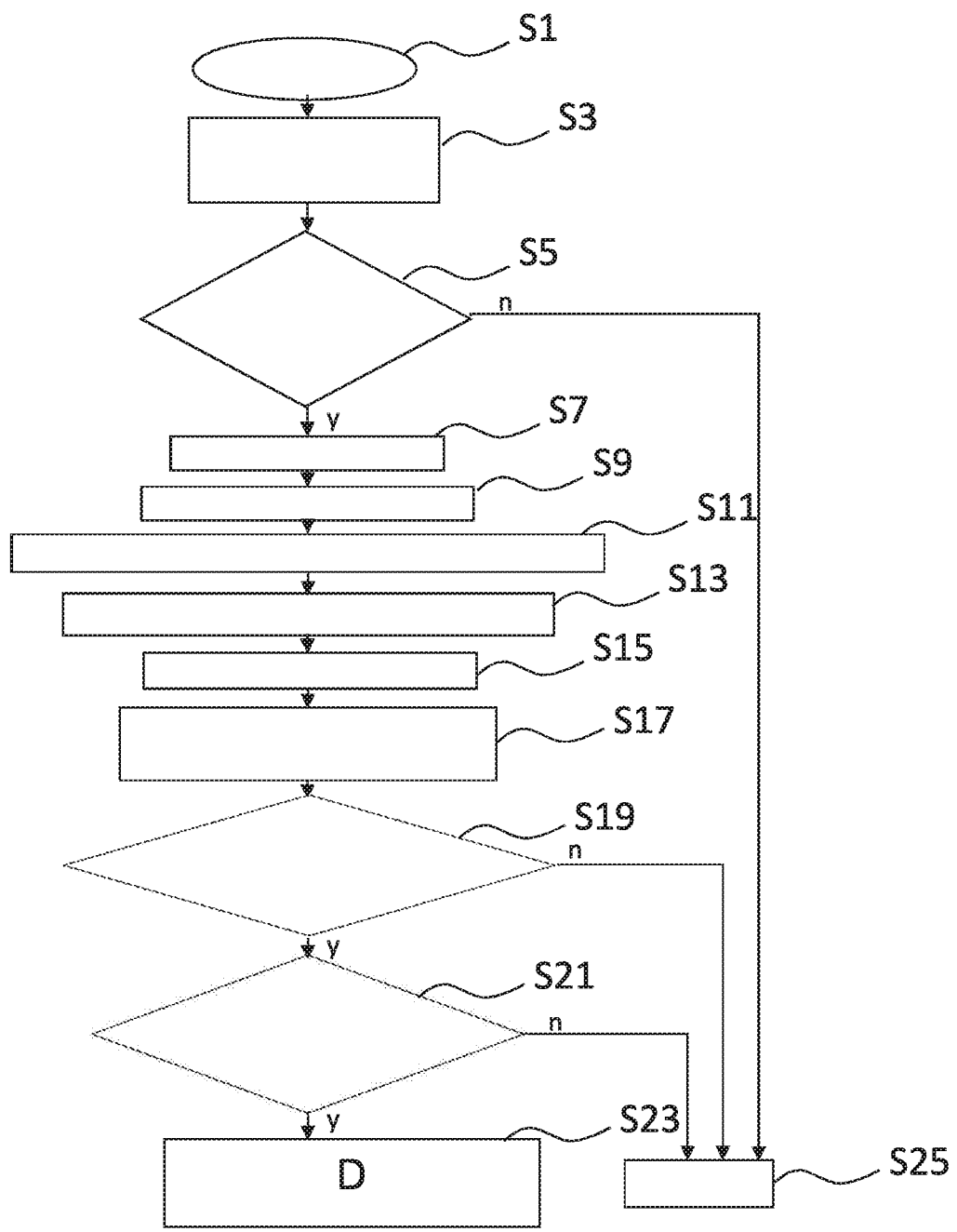
FIG. 2 shows a flow chart for operating the probe.

Alternatively to the flow chart represented in FIG. 2, for example steps S13 to S21 may be omitted if a valid self-diagnosis is ensured in another way. This is for example the case if the self-diagnosis is initiated by a control unit to which additionally information is provided about the engine operating state. In this case, it is ensured that the engine operating state does not change between the first point in time T1 and the fourth point in time T4, or else the self-diagnosis is terminated. Similarly, steps S3 to S7 could alternatively be omitted if it is ensured by the control unit that the engine operating state is unchanged between the third point in time T3 and the sixth point in time T6, or else the self-diagnosis is terminated.

The probe mentioned in the exemplary embodiment is in particular a nitrogen oxide probe. In other exemplary embodiments, it may also be a lambda probe for detecting an oxygen concentration.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for performing a self-diagnosis of a nitrogen oxide probe or a lambda probe with a pumped reference cell, comprising the steps of:
   providing a first point in time;
   providing a reference cell;
   providing a predetermined first time window, the first point in time being the beginning of the predetermined first time window;
   providing a second point in time;
   providing a third point in time, which is after the second point in time;
   providing a second predetermined time window, the third point in time being the beginning of the second predetermined time window; and
   providing a diagnostic characteristic value that is representative of an error in the determination of the oxides of nitrogen concentration;
   placing the reference cell into a pumped operating state;
   determining the first point in time by applying a pulse width modulated pump current to the reference cell;
   determining at least one first voltage characteristic value that is representative of a voltage applied to the reference cell within the predetermined first time window, such that the first voltage characteristic value is determined during a switched-off time of the pulse width modulated current;
   turning off the pulse width modulated pump current applied to the reference cell at the second point in time;
   determining the third point in time after the pulse width modulated pump current applied to the reference cell is turned off and the reference cell is in an unpumped operating state;
   determining at least one second voltage characteristic value that is representative of the voltage applied to the reference cell within the second predetermined time window;

determining the diagnostic characteristic value by determining the difference between the at least one first voltage characteristic value and the at least one second voltage characteristic value.

2. The method of claim 1, further comprising the steps of providing a wait phase for a predetermined first period of time which is carried out between the second point in time and the third point in time.

3. The method of claim 1, further comprising the steps of:
providing a fourth point in time, the fourth point in time being after the third point in time;
turning off the pulse width modulated pump current applied to the reference cell at the fourth point in time.

4. The method of claim 3, further comprising the steps of:
providing a fifth point in time, the fifth point in time being after the fourth point in time;
providing at least one third voltage characteristic;
providing a third predetermined time window, the fifth point in time being the beginning of the predetermined third time window;
turning on the reference cell;
placing the reference cell into a pumped operating state;
applying a pulse width modulated pump current to the reference cell at the fifth point in time;
determining the at least one third voltage characteristic value that is representative of the voltage applied to the reference cell within the predetermined third time window.

5. The method of claim 4, further comprising the steps of providing a wait phase for a predetermined second period of time which is carried out between the fourth point in time and the fifth point in time.

6. The method of claim 4, further comprising the steps of determining the diagnostic characteristic value as a function of the at least one third voltage characteristic value.

7. The method of claim 4, further comprising the steps of determining the diagnostic characteristic value based on an average value of the respective voltage values.

8. The method of claim 4, further comprising the steps of determining the diagnostic characteristic value based on the determination of a standard deviation depending on the respective voltage characteristic values.

9. The method of claim 1, further comprising the steps of:
providing the probe to further comprise a measurement cell;
providing a target voltage characteristic value that is representative of a voltage applied to the measurement cell for measuring a gas concentration of a gas mixture delivered to the probe;
determining the target voltage characteristic value as a function of the diagnostic characteristic value;
applying current to the measurement cell;
controlling the current applied to the measurement cell such that the voltage applied to the measurement cell is set to the target voltage characteristic value.

10. The method of claim 1, further comprising the steps of:
providing the probe to be an oxygen sensor;
determining an oxygen concentration of a gas mixture delivered to the oxygen sensor as a function of the diagnostic characteristic value.

11. The method of claim 1, further comprising the steps of:
providing an internal combustion engine;
provide an exhaust duct in fluid communication with the internal combustion engine; and
the probe further comprising a nitrogen oxide sensor at least partially disposed in the exhaust duct;
determining the first point in time based on the operating state of the internal combustion engine;
determining a nitrogen oxide concentration of a gas mixture delivered to the oxides of nitrogen sensor as a function of the diagnostic characteristic value.

* * * * *